United States Patent
Bojarski et al.

(10) Patent No.: US 9,188,528 B2
(45) Date of Patent: Nov. 17, 2015

(54) SENSOR FOR MONITORING A MEDIUM

(75) Inventors: Aldo Bojarski, Höckendorf (DE); Klaus Erler, Lübeck (DE); Katrin Künzelmann, Dresden (DE); Andre Legner, Dresden (DE); Paul Smith, Cambridge (GB); Tobby Strassberger, Höckendorf (DE)

(73) Assignee: AB Elektronik Sachsen GmbH, Klingenberg (DE)

( * ) Notice: Subject to any disclaimer, the term of this patent is extended or adjusted under 35 U.S.C. 154(b) by 210 days.

(21) Appl. No.: 13/824,413

(22) PCT Filed: Sep. 16, 2011

(86) PCT No.: PCT/EP2011/066126
§ 371 (c)(1),
(2), (4) Date: Jun. 4, 2013

(87) PCT Pub. No.: WO2012/038346
PCT Pub. Date: Mar. 29, 2012

(65) Prior Publication Data
US 2015/0036125 A1 Feb. 5, 2015

(30) Foreign Application Priority Data

Sep. 21, 2010 (DE) .......................... 10 2010 041 136
Sep. 21, 2010 (DE) ...................... 20 2010 012 769 U

(51) Int. Cl.
*G01N 21/41* (2006.01)

(52) U.S. Cl.
CPC ............ *G01N 21/4133* (2013.01); *G01N 21/41* (2013.01); *G01N 2201/0221* (2013.01)

(58) Field of Classification Search
CPC G01N 21/41; G01N 21/4133; G01N 21/4153
See application file for complete search history.

(56) References Cited

U.S. PATENT DOCUMENTS 4,884,065 A    11/1989   Crouse et al.
7,268,864 B2 *   9/2007   Chiarello et al. ............. 356/128

(Continued)

FOREIGN PATENT DOCUMENTS

DE    10 2007010 805 B3    10/2008
DE    10 2008 056 559 A1    5/2010

(Continued)

*Primary Examiner* — Gregory J Toatley
*Assistant Examiner* — Hina F Ayub
(74) *Attorney, Agent, or Firm* — Gudrun E. Huckett

(57) ABSTRACT

The invention relates to sensors for monitoring a medium, comprising an electromagnetic radiation source and a detector of electromagnetic radiation, the medium being located in the ray path between the electromagnetic radiation source and the detector and the refraction varying when the medium varies. The sensors are characterized by their ease of production. To that end, the electromagnetic radiation source and detector are disposed in at least one housing. Furthermore, either at least one region or at least one component of the housing consists of material which is transparent to electromagnetic radiation, the medium being located in the region or at the component of the housing. At least one wall of the region is so disposed or designed that the radiation for refraction impinges on or emerges from the surface at an angle which is different from 90°. In addition, the detector is at least one photo diode, such that, when the medium varies, the radiation either does not impinge or impinges on the photo diode.

2 Claims, 1 Drawing Sheet

(56) References Cited

U.S. PATENT DOCUMENTS

2008/0239317 A1* 10/2008 Schulkin et al. ............. 356/365
2009/0103076 A1   4/2009 Gloeckner
2009/0122300 A1   5/2009 Wu et al.
2011/0249257 A1  10/2011 Wildschuetz

FOREIGN PATENT DOCUMENTS

| EP | 0 337 173 A2 | 10/1998 |
| JP | 50 017147 B | 6/1975 |
| JP | 1 197632 A | 9/1989 |

* cited by examiner

SENSOR FOR MONITORING A MEDIUM

BACKGROUND OF THE INVENTION

The invention concerns sensors for monitoring a medium, comprising an electromagnetic radiation source and a detector for electromagnetic radiation wherein the medium is located in the beam path between the electromagnetic radiation source and the detector and the refraction changes upon change of the medium.

The publication DE 10 2007 010 805 B3 discloses a method and a device for determining the urea concentration of a solution. For this purpose, light is emitted at various incident angles onto a boundary surface between a denser medium and a less dense medium, i.e., the body and the solution. For this purpose, a boundary surface between the body and the solution must be present. The light is then partially reflected at the boundary surface, depending on the incident angle, wherein with increasing incident angle the proportion of light reflected at the boundary surface increases. The reflected radiation is then detected by an appropriately arranged spatially resolving radiation detector.

The publication DE 10 2008 056 559 A1 comprises a sensor arrangement for detection of a first liquid medium in a second liquid medium by means of reflection of an emitted light beam as well as a correlated receiver. For this purpose, two glass rod lenses encapsulated in a housing are arranged parallel to each other. The glass rod lenses have a different optical refractive index than the liquid media. Opposite the glass rod lenses a reflection surface is arranged that is connected to the housing.

It is disadvantageous that depositions and contaminations of the boundary surface or of the reflection surface can falsify the measured result.

SUMMARY OF THE INVENTION

The invention has the object to monitor the material composition of a medium in a simple way.

This object is solved in that the electromagnetic radiation source and the detector are arranged in at least one housing, in that either at least one area or at least one component of the housing is comprised of material transparent for the radiation of the electromagnetic radiation source, in that the medium is located at the area or at the component of the housing, in that at least one wall of the area is arranged or configured such that the radiation for refraction impinges on the surface or exits from it at an angle that is different from 90 degrees and is refracted thereby, and in that the detector is at least one photo diode so that upon a change of the medium the radiation either does not reach the photo diode or reaches the photo diode.

The sensors for monitoring a medium comprising an electromagnetic radiation source and a detector for electromagnetic radiation, wherein the medium is in the beam path between the electromagnetic radiation source and the detector and the refraction changes upon change of the medium, are characterized by their simple realization.

For this purpose, the electromagnetic radiation source and the detector are arranged in at least one housing. Moreover, either at least one area or at least one component of the housing is comprised of material that is transparent for electromagnetic radiation wherein medium is located at the area or at the component of the housing. At least one wall of the area is arranged or embodied such that the radiation for refraction impinges on the surface or exits from it at an angle different from 90 degrees. Moreover, the detector is at least one photo diode so that upon change of the medium the radiation either does not reach the photo diode or reaches the photo diode.

By means of the sensor, medium is monitored by means of the transmitted light principle. Upon change of the medium, the refractive index of the medium changes and as a result also the refractive angle. The position of the radiation relative to the detector shifts. Radiation impinging or no radiation impinging on the detector represents a measure for the change of the medium. This state is detected and can be signaled. The magnitude of the change is determined by means of the size of the chip of the photo diode. After a correction of the medium, the radiation will impinge again on the photo diode so that the normal state is reached.

These states, radiation reaching or not reaching the photo diode, can be signaled in a simple way acoustically and/or optically, as is known, by a control unit.

A further advantage resides in that contaminations on the housing that otherwise cause an intensity change have no effect on the detection. The same holds true for components in the medium that will make the medium turbid. Decisive for the detection is the incident location of the electromagnetic radiation and not its intensity. Therefore, aging processes of the radiation source and of the detector have no effect on the sensor for monitoring a medium.

In this way, a simple sensor is realized for monitoring a medium that changes its refractive index upon a change.

Moreover, the sensor is characterized in that only the medium is outside of the housing. All components of the sensor are arranged in the housing so that a compact sensor is provided. In the simplest case, for this purpose the electromagnetic radiation source and the detector are arranged opposite each other wherein a space for the medium is provided therebetween.

Advantageous embodiments of the invention are provided in the dependent claims.

The detector is comprised of photo diodes that are arranged in a row or a matrix so that the location of the electromagnetic radiation impinging on the detector can be detected based on the position of the photo diodes and based on this the medium and a change of the medium can be detected. The number, size, and the spacings of the photo diodes determine the precision of the sensor. The sensor for this purpose is a known array. Accordingly, in particular also the degrees of non-coincidence can be detected. The precision is significantly improved in comparison to the use of a single photo diode.

In the beam path down stream of the electromagnetic radiation source at least one device for guiding and/or deflecting the radiation is arranged so that the electromagnetic radiation source and the detector can be positioned adjacent to each other. The configuration is simplified significantly. The electromagnetic radiation source and the detector can be placed adjacent to each other on a carrier.

Expediently, mirrors or prisms are the radiation-deflecting device so that the radiation is deflected twice in sequence. The electromagnetic radiation source is advantageously arranged relative to the medium above the detector. The medium is located between the device and the detector. In this way, a very simple and compact configuration is provided for the sensor.

The device guiding the radiation is a light-wave conductor. When the light-wave conductor has preferably a U-shape for this purpose, the radiation of the electromagnetic radiation source impinges onto the adjacently positioned detector.

According to one embodiment, a first part of the housing is a cup-shaped formed part that is comprised of material transparent for the radiation. The first part has moreover a recess or a cutout for the medium. At least one wall of the cutout as an area of the housing 5 is arranged or embodied such that the radiation for refraction impinges on the surface or exits therefrom at an angle different from 90 degrees. The housing is closed off by a cover as a second part of the housing. In the first part at least the electromagnetic radiation source and the detector are arranged. The area of the housing with the recess or with the cutout is positioned in the medium so that the medium is also located in the recess or the cutout. By means of oppositely positioned wall areas of the recess or the cutout, the radiation is coupled out and after passing through the medium coupled in.

Beneficially, the formed part is monolithically embodied. In this way, it is possible to provide sensors that can be economically beneficially realized.

The detector is a one-dimensional or two-dimensional sensor. Moreover, the electromagnetic radiation source and the sensor are arranged adjacent to each other on a carrier so that a signal that can be correlated with a location of the incident electromagnetic radiation can be detected.

The sensor is connected with a data processing system for determining the location of the radiation impinging on the sensor based on the position of the photo diodes. The data processing system is a known microcomputer.

Advantageously, the medium is an aqueous solution so that the concentration of at least one substance in the aqueous solution can be detected.

BRIEF DESCRIPTION OF THE DRAWINGS

One embodiment of the invention is disclosed in the drawings in principle, respectively, and will be explained in the following in more detail.

It is shown in.

DESCRIPTION OF PREFERRED EMBODIMENTS

The sensor for monitoring a medium is comprised substantially of an electromagnetic radiation source 1, a detector 2, a device 3 deflecting the radiation, and a housing 5.

Figure 1:
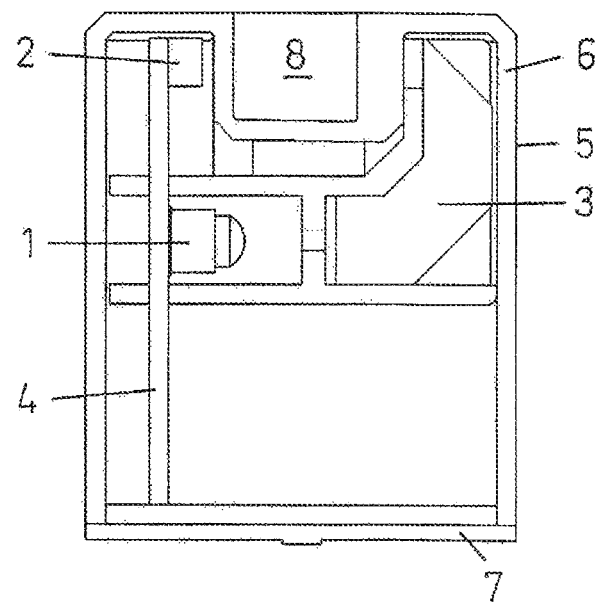
FIG. 1 a sensor for monitoring a medium in a longitudinal section.

FIG. 1 shows a sensor for monitoring a medium in a longitudinal section in a principal illustration.

The medium is for example an aqueous solution. As is known, as the electromagnetic radiation source 1 a luminescence diode 1 and as the detector 2 a CCD sensor 2 with photo diodes is used wherein CCD stands for charge-coupled device. It is embodied as a one-dimensional (line) or two-dimensional (matrix) CCD sensor 2.

The luminescence diode 1 and CCD sensor 2 are arranged adjacent to each other on a circuit board 4 as carrier 4.

The circuit board 4 is arranged in a first part 6 of the housing 5. This first part 6 is cup-shaped and is comprised of a material that is transparent for the radiation of the luminescence diode 1. Moreover, this first part 6 is a monolithically embodied formed part which has a cutout 8/a recess for the medium.

In the beam path downstream of the luminescent diode 1, the radiation-deflecting device 3 with two prisms or mirrors is arranged so that the radiation is deflected in sequence twice by 90 degrees. The entry of the device 3 is arranged in the plane of the luminescent diode 1 so that its electromagnetic radiation can be coupled into the device 3. The exit for coupling out the electromagnetic radiation of the luminescent diode 1 that has been twice deflected by 90 degrees is arranged in the plane of the CCD sensor 2. Between the device 3 and the CCD sensor 2, there is the cutout 8 for the medium so that through the wall areas of the cutout the electromagnetic radiation penetrates these wall areas and the space formed by the space of the cutout 8. At least one wall of the cutout 8 is arranged or embodied such that the radiation impinges on the surface or exits from it at an angle different from 90 degrees for refraction. For this purpose, for example a plate-shaped wall with an angle different from 90 degrees is arranged relative to the radiation or this wall is wedge-shaped.

In the situation of use, the medium is located in this cutout 8 so that the radiation penetrates the medium contained in the cutout.

Advantageously, the optical elements are arranged such that the radiation in the normal situation reaches the CCD sensor 2 centrally. When the composition of the medium changes, its refractive index will also change and thus its refractive angle. The radiation of the luminescent diode 1 reaches a location that is different from that of the normal situation and thus a different photo diode of the CCD sensor 2.

The location and thus the position can be detected and signaled.

In a first embodiment, the luminescent diode 1 is arranged spaced relative to the medium above the CCD sensor 2 (illustration in FIG. 1).

In a second embodiment, the luminescent diode 1 is arranged at a spacing adjacent to the CCD sensor 2.

Figure 2:
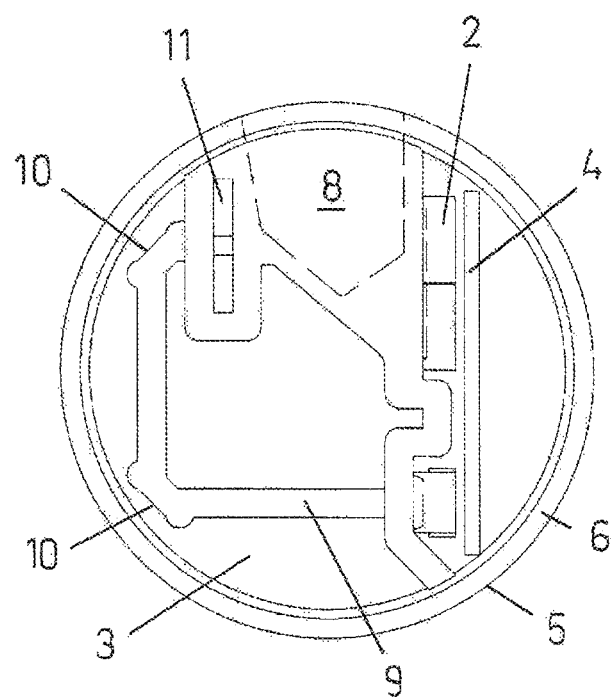
FIG. 2 a sensor in a section illustration.

FIG. 2 shows for this purpose a sensor in a principal section illustration.

In the beam path downstream of the luminescent diode 1 the radiation-deflecting device 3 with the devices 10 for reflecting the radiation in the form of mirrors 10 is arranged in a light-guiding passage 9 so that the radiation in sequence is deflected twice by 90 degrees. The radiation-deflecting device 3 and the first part 6 of the housing 5 are either embodied in a multi-part or single-part configuration. The luminescent diode 1, the CCD sensor 2, the device 3 and the cutout 8 are located in a plane. In a variant of this second embodiment, a slit diaphragm 11 is a component of the device 3.

The second part 7 of the housing 5 is a cover 7 so that an overall enclosed sensor for monitoring the medium can be realized.

In a further embodiment, the CCD sensor 2 is connected with a data processing system for determining the location of the radiation that has reached the CCD sensor 2 based on the position of the luminescent diodes. The data processing system is for this purpose a known microcontroller and is advantageously located on the circuit board 4.

What is claimed is:

1. Sensor for monitoring a medium, the sensor comprising:

an electromagnetic radiation source;

a detector for electromagnetic radiation, the detector comprised of photo diodes, wherein the medium is located in the beam path between the electromagnetic radiation source and the detector and the refraction changes upon change of the medium;

a two-part housing comprised of a first part (6) and of a second part (7), wherein the first part (6) is a cup-shaped monolithic part comprised of material that is transparent for the radiation of the electromagnetic radiation source and provided with an outwardly open cutout (8) for accommodating the medium, wherein the cup-shaped monolithic part comprises an interior, wherein the electromagnetic radiation source (1) and the detector (2) are arranged in the interior of the cup-shaped monolithic part;

mirrors (10) arranged in the interior of the housing downstream of the electromagnetic radiation source in the beam path of the radiation, the mirrors deflecting the radiation twice in sequence and the electromagnetic radiation source (1) and the detector (2) placed adjacent to each other in the interior of the housing;

wherein the cup-shaped monolithic part comprises at least one plate-shaped wall that forms part of the outwardly open cutout (8), wherein the at least one plate-shaped wall is arranged at an angle different from 90 degrees relative to the beam path of the radiation;

wherein the second part (7) is a cover (7) closing off the interior of the cup-shaped monolithically formed part (6);

wherein the photo diodes are arranged in a row or a matrix;

wherein the detector (2) is connected with a data processing system for determining the location of the electromagnetic radiation that has reached the detector (2) based on the position of the photo diodes of the detector (2).

2. Sensor according to claim 1, characterized in that the medium is an aqueous solution so that the concentration of at least one substance in the aqueous solution can be detected.

\* \* \* \* \*